United States Patent
Tanaka et al.

(10) Patent No.: US 10,302,566 B2
(45) Date of Patent: May 28, 2019

(54) METHOD FOR EVALUATING PHYSICAL PROPERTIES OF POLYMER COMPOSITIONS

(71) Applicants: Kyushu University, Fukuoka (JP); Fuji Electric Co., Ltd., Kanagawa (JP)

(72) Inventors: Keiji Tanaka, Fukuoka (JP); Daisuke Kawaguchi, Fukuoka (JP); Atsuomi Shundo, Fukuoka (JP); Mika Aoki, Fukuoka (JP); Tatsuya Ganbe, Kanagawa (JP); Nobuyuki Sekine, Kanagawa (JP); Kenji Okamoto, Kanagawa (JP)

(73) Assignees: Kyushu University (JP); Fuji Electric Co., Ltd. (JP)

( * ) Notice: Subject to any disclaimer, the term of this patent is extended or adjusted under 35 U.S.C. 154(b) by 149 days.

(21) Appl. No.: 15/035,705

(22) PCT Filed: May 8, 2015

(86) PCT No.: PCT/JP2015/063300
§ 371 (c)(1),
(2) Date: May 10, 2016

(87) PCT Pub. No.: WO2015/174338
PCT Pub. Date: Nov. 19, 2015

(65) Prior Publication Data
US 2016/0282267 A1    Sep. 29, 2016

(30) Foreign Application Priority Data
May 14, 2014    (JP) ................. 2014-100654

(51) Int. Cl.
*G01N 21/64*    (2006.01)

(52) U.S. Cl.
CPC ....... *G01N 21/6408* (2013.01); *G01N 21/648* (2013.01); *G01N 21/6428* (2013.01)

(58) Field of Classification Search
CPC .................................................. G01N 21/6408
See application file for complete search history.

(56) References Cited

U.S. PATENT DOCUMENTS

2003/0128737 A1*    7/2003    McGrath ................. G01K 11/20
                                                                    374/161
2004/0178734 A1*    9/2004    Nagasaki ................. C03C 8/02
                                                                    313/634
(Continued)

FOREIGN PATENT DOCUMENTS

CN    103558201 A    *    2/2014    ............. G01N 21/64
JP        2772116 B2          7/1998
(Continued)

OTHER PUBLICATIONS

Melby et al., "Synthesis and Fluorescence of Some Trivalent Lanthanide Complexes", Dec. 1964, Journal of the American Chemical Society, vol. 86, pp. 5117-5125.*

(Continued)

*Primary Examiner* — David P Porta
*Assistant Examiner* — Jeremy S Valentiner
(74) *Attorney, Agent, or Firm* — Lerner, David, Littenberg, Krumholz & Mentlik, LLP (57) ABSTRACT

A method evaluates the mobility of a polymer composition in a high-temperature region of 150° C. or above. The method for evaluating a physical property of a polymer composition, the method comprising the steps of: obtaining a thin film sample which is formed on a substrate and which comprises: a fluorescent probe including a fluorescent rare earth complex having a melting point of 200° C. or higher; and a target polymer composition; and obtaining a relationship between a temperature and a fluorescent characteristic of the thin film.

13 Claims, 2 Drawing Sheets

(56) References Cited

U.S. PATENT DOCUMENTS

| | | | | |
|---|---|---|---|---|
| 2011/0250406 A1* | 10/2011 | Zia | ............ | C09K 11/02 428/174 |
| 2012/0190123 A1 | 7/2012 | Hasegawa et al. | | |
| 2015/0152322 A1* | 6/2015 | Nakayama | ............ | C09K 9/02 252/301.35 |

FOREIGN PATENT DOCUMENTS

| | | |
|---|---|---|
| JP | 2009242385 A | 10/2009 |
| JP | 5414073 B2 | 2/2014 |

OTHER PUBLICATIONS

Zhang et al., "Electrospinning Preparation and Photoluminescence Properties of Rare-Earth Complex/Polymer Composite Fibers", Apr. 2007, Journal of Physical Chemistry, vol. 111, No. 17, pp. 6524-6527.*

English Translation—Bao et al.—CN 103558201 A—obtained from Google Patents on Sep. 19, 2018 (Year: 2014).*

Keiji Tanaka et al., Interfacial Mobility of Polymers on Inorganic Solids, J.Phys.Chem.B, 2009, vol. 113 No. 14, pp. 4571-4577.

Atsuomi Shundo et al., Fluorescence Behavior of Dyes in Thin Films of Various Polymers, Macromolecules, 2012, vol. 45 No. 1, pp. 329-335.

Christopher J.Ellison et al., The distribution of glass-transition temperatures in nanoscopically confined glass formers, nature materials, Oct. 2003, vol. 2, pp. 695-700.

International Search Report for Application No. PCT/JP2015/063300 dated Jul. 14, 2015.

Y. Nishijima, Berichte Der Bunsen-Gesellschaft Fur Physikalische Chemie, Studies on the Structure Change of Polymer Solids by the Fluorescence Methods, 74, 778 (1970).

Daisuke Kawaguchi et al., "Structures and Physical Properties at Surfaces and Interfaces of Polymers", Journal of Japanese Society of Tribologists, Oct. 15, 2013 (Oct. 15, 2013), vol. 58, No. 10, pp. 44 to 51.

* cited by examiner

METHOD FOR EVALUATING PHYSICAL PROPERTIES OF POLYMER COMPOSITIONS

CROSS-REFERENCE TO RELATED APPLICATION

The present application is a national phase entry under 35 U.S.C. § 371 of International Application No. PCT/JP2015/063300, filed May 8, 2015, which claims priority from Japanese Application No. 2014-100654, filed May 14, 2014 published in, all of which are incorporated herein by reference.

TECHNICAL FIELD

The present invention relates to a method for evaluating a physical property of a polymer composition. In particular, the present invention relates to a method for evaluating the thermal mobility of molecular chains of a polymer composition having a high glass transition temperature.

BACKGROUND ART

Thermoplastic resins and thermosetting resins made of polymer materials have been widely used in the industrial field, and are generally required to have characteristics such as heat resistance and toughness. These characteristics of polymer materials are generally dependent on the glass transition temperature ($T_g$), and the determination of $T_g$ values of various polymer materials has a great significance in terms of the design and production of industrial products. Conventionally, the $T_g$ of a polymer material has been determined based on the differential scanning calorimetry (DSC).

Recently, development of high performance materials by complexing a polymer and an inorganic filler has been active. Since the decrease in size and improvement in dispersibility of the inorganic filler lead to a remarkable increase in area of the interface between the polymer and the inorganic material, the physical properties at the interface may determine the physical properties of the material as a whole. Accordingly, the understanding of the thermal mobility of molecular chains at an interface with an inorganic material is an important issue to be studied.

The fluorescent probe method is widely known as an approach for investigating the dynamic environment of a matrix polymer by evaluating the fluorescence intensity, the fluorescence lifetime, and the rotational relaxation time as functions of the temperature (see, for example, Non-Patent Document 1). It is also known that, if probe molecules can be arranged with positional selectivity, the fluorescent probe method is extremely useful as an approach for space-resolved evaluation of the $T_g$ in a confined space such as a thin film or an interface with another kind of solid (see, for example, Non-Patent Documents 2 and 3). Until now, it has been revealed that the $T_g$ of polystyrene (PS) at an interface with an inorganic solid is remarkably higher than the bulk value based on an evanescent wave excitation fluorescence lifetime measurement (see, for example, Non-Patent Document 2).

PRIOR ART DOCUMENTS

Non-Patent Documents

[Non-Patent Document 1] Y. Nishijima, Berichte Der Bunsen-Gesellschaft Fur Physikalische Chemie, 74, 778 (1970)

[Non-Patent Document 2] J. Phys. Chem. B 2009, 113, 4571-4577

[Non-Patent Document 3] Macromolecules 2012, 45, 329-335

SUMMARY OF INVENTION

Technical Problems

However, conventionally used fluorescent probes made of organic dyes have limitations in terms of heat stability, and are thermally decomposed at around 100 to 150° C., in general. Accordingly, there has been such a problem that the fluorescent probe method using an organic dye cannot be applied to a polymer having a high $T_g$ of about 150° C. or higher. For this reason, inconveniently, the method for measuring the bulk $T_g$ of a polymer having a high $T_g$ is limited to the DSC measurement. In addition, no method has been established for measuring the $T_g$ at an interface between a polymer having a high $T_g$ and another type of solid.

Meanwhile, in the field of electronics and the like, resins have been required to have increasingly higher heat resistance, and the importance of evaluation of characteristics of a polymer composition having a high $T_g$ has been highly recognized.

To widen the application of the conventional fluorescent probe method to the high-temperature region, the present inventors have focused on fluorescent rare earth complexes chemically stable even at high temperatures as novel fluorescent probes. Whether the thermal motions of a matrix polymer are reflected on a fluorescent characteristic of a fluorescent rare earth complex has not been examined at all so far.

Solution to Problems

To solve the above-described problems, the present inventors have found that the use of a fluorescent rare earth complex which has a higher melting point than conventional organic dye compounds, which can be used even in a high-temperature region, and which exhibits a remarkable fluorescent characteristic as a fluorescent probe makes it possible to evaluate a physical property of a polymer composition not only in the bulk but also at an interface between the polymer composition and another kind of solid, which is non-polymer. This finding has led to the completion of the present invention.

The present invention provides a method for evaluating a physical property of a polymer composition, the method comprising the steps of: obtaining a thin film sample which is formed on a substrate and which comprises: a fluorescent probe including a fluorescent rare earth complex having a melting point of 200° C. or higher; and a target polymer composition; and obtaining a relationship between a temperature and a fluorescent characteristic of the thin film sample.

In the above-described method for evaluating a polymer composition, the fluorescent probe preferably comprises a fluorescent rare earth complex containing a trivalent lanthanoid ion as a central metal ion.

In an embodiment of the above-described method for evaluating a polymer composition, the fluorescent probe is uniformly dispersed in the thin film sample, and, in the step of obtaining the relationship, the fluorescent characteristic is an intensity ratio between a fluorescence intensity of electric dipole transition of the target polymer composition and a fluorescence intensity of magnetic dipole transition of the target polymer composition, and a bulk glass transition temperature of the target polymer composition can be obtained from a correlation between the temperature of the thin film sample and the intensity ratio.

In another embodiment of the above-described method for evaluating a polymer composition, the fluorescent probe is uniformly dispersed in the thin film sample, and, in the step of obtaining the relationship, the fluorescent characteristic is a fluorescence lifetime, and a glass transition temperature at an interface between the target polymer composition and the substrate can be obtained from a correlation between the temperature of the thin film sample and the fluorescence lifetime.

In the method in which the fluorescent characteristic is a fluorescence lifetime, the fluorescence lifetime is preferably an evanescent excitation fluorescence lifetime.

In still another embodiment of the above-described method for evaluating a polymer composition, the fluorescent probe in the thin film sample is localized at a predetermined distance from an interface with the substrate, and, in the step of obtaining the relationship, the fluorescent characteristic is a fluorescence lifetime, and a glass transition temperature of the target polymer composition at the predetermined distance from the interface between the target polymer composition and the substrate can be obtained from a correlation between the temperature of the thin film sample and the fluorescence lifetime.

Another aspect of the present invention provides a fluorescent probe used in a method including: forming a thin film sample including a fluorescent probe and a target polymer composition on a substrate; determining a relationship between a temperature and a fluorescent characteristic of the thin film sample; and determining a physical property of the target polymer composition on the basis of the relationship, the fluorescent probe comprising a fluorescent rare earth complex having a melting point of 200° C. or higher.

Another aspect of the present invention provides a thin film sample used in a method including: forming a thin film sample including a fluorescent probe and a target polymer composition on a substrate; determining a relationship between a temperature and a fluorescent characteristic of the thin film sample; and determining a physical property of the target polymer composition on the basis of the relationship, the thin film sample comprising: a fluorescent probe including a fluorescent rare earth complex having a melting point of 200° C. or higher; and a target polymer composition.

In a mode, the fluorescent probe is uniformly dispersed in the thin film sample.

In another mode, the fluorescent probe in the thin film sample is localized at a predetermined distance from an interface with the substrate.

Another aspect of the present invention provides an apparatus for determining a bulk glass transition temperature of a polymer composition, the apparatus comprising: a heater configured to heat the thin film sample; an apparatus configured to measure a fluorescence spectrum of the thin film sample; and optionally a computation processing unit. This apparatus can be used to carry out the above-described method in which the fluorescent characteristic is a fluorescence intensity ratio.

Another aspect of the present invention provides an apparatus for determining an interface-dependent glass transition temperature of a polymer composition, the apparatus comprising: a heater configured to heat the thin film sample; an apparatus configured to measure a fluorescence lifetime of the thin film sample; and optionally a computation processing unit. The apparatus can be used to carry out the above-described method in which the fluorescent characteristic is a fluorescence lifetime.

Advantageous Effects of Invention

The method for evaluating a physical property of a polymer composition according to the present invention, in which the fluorescent rare earth complex is used as a fluorescent probe, makes it possible to easily determine the $T_g$ of a polymer composition having a $T_g$ in a high-temperature region of 150° C. or above, which cannot be measured by any conventional fluorescent probe method, by using a thin film sample. In addition, it is also possible to determine the $T_g$ at an interface between a polymer composition and another kind of solid constituting a substrate and the $T_g$ dependent on the interface with the other type of solid at a predetermined distance from the substrate, both of which also cannot be measured by any conventional fluorescent probe method.

DESCRIPTION OF EMBODIMENTS

Hereinafter, embodiments of the present invention are described. However, the present invention is not limited to the embodiments described below.

First Embodiment: Evaluation of Glass Transition Temperature of Polymer Composition in Bulk (Inside Film)

The present invention provides, in a first embodiment, a method for evaluating a physical property of a polymer composition in a bulk, the method comprising the steps of: obtaining a thin film sample which is formed on a substrate and which comprises at least: a fluorescent probe including a fluorescent rare earth complex having a melting point of 200° C. or higher; and a target polymer composition; and obtaining a relationship between a temperature and a fluorescence intensity of the thin film sample.

(1) Step of Obtaining Thin Film Sample

A first step in the first embodiment is the step of obtaining a thin film sample. The thin film sample in the first embodiment contains at least a target polymer composition and a fluorescent probe including a fluorescent rare earth complex. The fluorescent probe is uniformly dispersed in the thin film. The target polymer composition means a polymer composition to be determined for the glass transition temperature, and refers to a composition containing an amorphous polymer, in general. Accordingly, the target polymer composition may be made of a polymer compound, or may be a mixture of two or more different polymer compounds. The target polymer composition also may be a mixture of a polymer compound and a low molecular weight compound. Note, however, that the target polymer composition has to have a $T_g$ which is lower than the thermal decomposition temperature (5% weight loss temperature) of the fluorescent probe, described in detail later. In addition, colored polymer compositions, which disturb the measurement of the fluorescence intensity, cannot be measured in the first embodiment.

As the fluorescent probe, a fluorescent rare earth complex having a melting point of 200° C. or higher can be used. In particular, the fluorescent probe may be a fluorescent rare earth complex of which the fluorescence spectrum has a peak in the visible or ultraviolet region.

As the central metal ion constituting the fluorescent rare earth complex, for example, it is preferable to use any trivalent lanthanoid ion selected from $Ce^{3+}$, $Nd^{3+}$, $Sm^{3+}$, $Eu^{3+}$, $Tb^{3+}$, $Dy^{3+}$, $Er^{3+}$, and $Yb^{3+}$. Of these trivalent lanthanoid ions, $Nd^{3+}$, $Eu^{3+}$, $Tb^{3+}$, and $Dy^{3+}$ are preferable. This is because the radiationless transition is less likely to occur, and the fluorescence quantum yield is high, so that these trivalent lanthanoid ions exhibit strong fluorescence.

Specific fluorescent rare earth complexes include sodium [4'-(4'-amino-4-biphenylyl)-2,2':6',2''-terpyridine-6,6''-diyl-bis(methyliminodiacetato)]europate(III), europium(III) chloride hexahydrate, (1,10-phenanthroline)tris[4,4,4-trifluoro-1-(2-thienyl)-1,3-butanedionato]europium(III), tris(1,3-diphenyl-1,3-propanedionato)(1,10-phenanthroline)europium(III), tris(2,2,6,6-tetramethyl-3,5-heptanedionato)europium(III), neodymium(III) acetylacetonate hydrate, neodymium(III) triisopropoxide neodymium(III) nitrate hexahydrate, neodymium(III) chloride hexahydrate, neodymium(III) nitrate hydrate, neodymium(III) carbonate hydrate, neodymium(III) trifluoromethanesulfonate, neodymium(III) fluoride, tris[N,N-bis(trimethylsilyl)amide] neodymium(III), terbium(III) acetylacetonate hydrate, terbium(III) tris(2,2,6,6-tetramethyl-3,5-heptanedionate), terbium(III) nitrate pentahydrate, terbium(III) nitrate hexahydrate, and terbium(III) acetate hydrate. Of these fluorescent rare earth complexes, tris(1,3-diphenyl-1,3-propanedionato)(1,10-phenanthroline)europium(III) is preferable. However, the fluorescent rare earth complexes are not limited to these examples.

Note that the fluorescent rare earth complex used as the fluorescent probe is determined considering also the relationship with the target polymer composition to be measured, and it is preferable to select a fluorescent rare earth complex of which the fluorescence wavelength does not overlap with that of the target polymer composition to be measured.

In the first embodiment, the fluorescent rare earth complex used as the fluorescent probe is preferably contained at 3 to 30% by mass, where the total mass of the polymer composition and the fluorescent probe constituting the thin film sample is taken as 100%. The content is more preferably 4 to 20% by mass, and most preferably 5 to 10% by mass. This is because the fluorescent rare earth complex at such a content provides a fluorescence intensity enough to be analyzed, without affecting the molecular motions of the target polymer composition. In addition, in the thin film, the fluorescent rare earth complex is preferably uniformly dispersed in the polymer composition.

A method for forming the thin film sample to be measured may be based on a solvent evaporation method. The solvent evaporation method is advantageous in that a film with a thickness of from several hundred nanometers to several tens of micrometers can be formed. Specifically, the film can be formed by dissolving the target polymer composition and the fluorescent rare earth complex in a solvent in a uniformly dispersed manner, then applying the solution onto a substrate, and removing the solvent by evaporation. As the solvent, a solvent which is volatile and is a good solvent for both the target polymer composition and the fluorescent rare earth complex can be used. Examples of the solvent include, but are not limited to, toluene, chloroform, dichloromethane, tetrahydrofuran, ethyl acetate, acetone, and 1,4-dioxane.

In addition, the film can also be formed by a spin coating method. The spin coating method is advantageous in that a film with a thickness of from 100 nm to 1 μm can be formed. Specifically, the film can be formed by dissolving the target polymer composition and the fluorescent rare earth complex in a solvent in a uniformly dispersed manner, then dropping the solution onto a substrate, rotating the substrate at a high speed, and allowing the solvent to evaporate. Also in the spin coating method, the same solvents as those in the solvent evaporation method can be used.

Alternatively, when an uncured composition is liquid as in the case of a thermosetting resin such as an epoxy resin, the thin film can be formed without using any solvent. In this case, the thin film can be formed by an ordinary coating technique, for example, by screen printing or by shaping the thermosetting resin in which the fluorescent rare earth complex is dispersed by using any of various coaters capable of forming a thin film having a predetermined thickness described below and then curing the thermosetting resin. However, the coating technique is not limited to specific methods.

When the film is formed by dissolving the target polymer composition and the fluorescent rare earth complex in the solvent, the concentration is such that the total mass of the target polymer composition and the fluorescent rare earth complex is, for example, 1 to 10% by mass, and preferably 2 to 10%, where the total mass of the solution is taken as 100%. However, the concentration is not particularly limited.

Alternatively, the film can be formed by employing a vapor deposition method in some part. In this case, layers of the target polymer composition which are prepared by a solvent evaporation method and which have thicknesses of approximately 500 nm to 5 μm and vapor deposition layers which are made of the fluorescent rare earth complex and which have thicknesses of approximately 1 to 5 nm are alternately stacked on one another, so that the fluorescent rare earth complex can be present at the above-described concentration (% by mass) in the polymer composition as a whole.

The thin film containing the target polymer composition is formed on a substrate. In this embodiment, the substrate can be made of a substance which is transparent, which has no absorption in the wavelength region where the fluorescence spectrum of the fluorescent rare earth complex is observed, and which is thermally stable in the measurement temperature range. Here, the term, transparent, means that the light transmittance is 80% or higher, in general. Specific examples of the substrate on which the thin film can be formed include, but are not limited to, glass, sapphire prism, quartz prism, indium tin oxide, zinc oxide, and lithium niobate. In addition, the thickness of the substrate is preferably 0.1 to 10 mm, and more preferably 0.5 to 1 mm. However, the thickness is not limited to these values.

The thickness of the thin film formed on the substrate is such that the thickness after removal of the solvent by vacuum drying is preferably approximately 100 nm or more, and is preferably 100 nm to 100 μm and further preferably 100 nm to 10 μm. Note that the thickness of the thin film can be adjusted by changing the concentration of the solution and the amount of the solution dropped.

After formation as described above, the thin film is dried. The thin film is preferably dried under vacuum for 24 hours or more to completely remove the solvent. Simultaneously with the drying or separately from the drying step, the thin film is optionally subjected to a heat treatment at a temperature higher than an estimated $T_g$ of the target polymer composition by 30° C. or more. This heat treatment is conducted to relax a non-equilibrium state, which may be created in the polymer composition during the film formation by the solvent evaporation method.

The thus obtained thin film is used as a measurement sample in the next step. Note that, in this embodiment, the film formation step of forming a thin film containing a target polymer composition and a fluorescent probe on a specific substrate itself is not necessarily essential, as long as a thin film sample formed on a substrate and meeting the above-described conditions can be obtained.

(2) Step of Obtaining Correlation Between Fluorescence Intensity and Temperature The step of obtaining a correlation between a fluorescence intensity and a temperature comprises the steps of: measuring a fluorescence intensity of the thin film sample obtained in step (1) over a predetermined temperature range; and determining a Tg on the basis of the measurement results.

In the step of measuring a fluorescence intensity, the fluorescence intensity is measured at multiple temperatures by changing the temperature of the thin film sample over a range from about room temperature (approximately 25° C.) to a temperature which is higher than an estimated $T_g$ of the target polymer composition by 20 to 50° C., or by changing the temperature over a range from about a temperature which is lower than the $T_g$ by 80 to 100° C. to a temperature which is higher than the estimated $T_g$ of the target polymer composition by 20 to 50° C. To obtain approximate straight lines for calculating the $T_g$ more accurately, it is preferable to measure the fluorescence intensity over a wider temperature range. In general, the measurement is preferably conducted from the low-temperature side to the high-temperature side. A temperature control method is not particularly limited, as long as the temperature of the target polymer composition in the thin film sample can be controlled to the predetermined temperature, and the relationship between the temperature and the fluorescence intensity can be indicated sufficiently accurately. For example, the temperature can be controlled by using a ceramic heater having a built-in thermocouple. It is particularly preferable to control the heating by sandwiching the thin film sample between ceramic heaters from the above and below.

The measurement of the fluorescence intensity can be conducted by using an ordinary fluorescence spectrophotometer. In a low-temperature range of the above-described temperature range, i.e., in the range from room temperature to a temperature which is lower than the $T_g$ by 30 to 50° C., the fluorescence intensity is preferably measured at temperature intervals of, for example, 10 to 15° C. In a temperature region near the $T_g$, i.e., in the temperature range from a temperature lower than the $T_g$ by 30 to 50° C. to a temperature higher than the $T_g$ by 30 to 50° C., the fluorescence intensity is preferably measured at temperature intervals of, for example, 5 to 10° C. These are intended to obtain two approximate straight lines described later more accurately. Note that it is also possible to conduct the measurement at smaller temperature intervals for more accurate measurement.

Regarding the excitation wavelength for the measurement of the fluorescence intensity, a person skilled in the art can determine an optimum excitation wavelength, as appropriate, according to the type of the ligand of the fluorescent rare earth complex constituting the fluorescent probe by calculation or measurement of an absorption spectrum conduced beforehand.

The fluorescence intensity is measured in a certain wavelength range. The fluorescence intensity is measured at a wavelength at which the peak is the largest, but also at multiple wavelengths corresponding to multiple transitions. In particular, at least the fluorescence intensity at a wavelength corresponding to electric dipole transition and the fluorescence intensity at a wavelength corresponding to magnetic dipole transition are obtained. The wavelengths vary depending on the type of the central metal ion constituting the fluorescent rare earth complex. A person skilled in the art can assign peaks in the measured fluorescence spectra to the corresponding transitions.

Subsequently, a step of calculating the $T_g$ on the basis of the measurement results of the fluorescence intensity is conducted. Specifically, the step of calculating the $T_g$ comprises the steps of: calculating $R_T = I_{5D0 \to 7F2}/I_{5D0 \to 7F1}$, which is the ratio of the fluorescence intensity $I_{5D0 \to 7F2}$ at a wavelength corresponding to the electric dipole transition $^5D_0 \to {}^7F_2$ to the fluorescence intensity $I_{5D0 \to 7F1}$ at a wavelength corresponding to the magnetic dipole transition $^5D_0 \to {}^7F_1$ at each measuring temperature; plotting the $R_T$ against the temperature T (° C.); obtaining an approximate straight line in the high-temperature region and an approximate straight line in the low-temperature region on the basis of the plotted results; and obtaining, as the $T_g$, an intersection between the approximate straight line in the high-temperature region and the approximate straight line in the low-temperature region.

The step of obtaining the approximate straight line in the high-temperature region and the approximate straight line in the low-temperature region can be conducted by obtaining approximate straight lines in each region by the least-squares method and employing one with the smallest error.

This step is a step of analyzing the data obtained in the step of measuring a fluorescence intensity, and, if necessary, the data can be analyzed by using a computation processing unit such as a computer connected to the fluorescence spectrophotometer.

According to this embodiment, the bulk glass transition temperature of a polymer composition with a high $T_g$ can be obtained by a simple method. The method of this embodiment is advantageous in that the $T_g$ of a sample with an extremely small thickness of approximately 100 nm at the smallest can be measured, and that the $T_g$ can be measured even when the amount of the polymer composition is very small, in comparison with the DSC measurement known as a technique for measuring the $T_g$ of a resin from the past. In addition, the method of this embodiment is advantageous also in that the $T_g$ of a specific substance in a mixed state can be measured by segregation of the fluorescent probe in a component in a polymer composition containing two or more components.

The temperature dependence of the fluorescence intensity of the fluorescent rare earth complex is so high that each of the fluorescence intensities corresponding to the transitions greatly decreases at approximately 300 to approximately 420° C., which are within the measurement range. Hence, the information on the molecular motions of the polymer composition constituting the film cannot be extracted simply based on the information on the absolute value of the fluorescence intensity at the wavelength at which the peak is largest alone. In this respect, this embodiment is advantageous in that the intensity ratio is used to extract the information on the molecular motions, making it possible to obtain the $T_g$.

Another aspect of this embodiment provides an apparatus for determining a bulk glass transition temperature of a polymer composition, the apparatus comprising: a heater configured to heat the thin film sample, an apparatus configured to measure a fluorescence spectrum of the thin film sample, and optionally a computation processing unit. The heater, the apparatus configured to measure a fluorescence spectrum, and the computation processing unit constituting this apparatus are the same as those described above, and the bulk glass transition temperature of a polymer composition can be obtained by operating this apparatus as described above.

Second Embodiment: Evaluation of Glass Transition Temperature of Polymer Composition at Interface The present invention provides, in a second embodiment, a method for evaluating a physical property of a polymer composition at an interface, the method comprising the steps of: obtaining a thin film sample which is formed on a substrate and which comprises at least: a fluorescent probe including a fluorescent rare earth complex having a melting point of 200° C. or higher; and a target polymer composition; and obtaining a relationship between a temperature and a fluorescence lifetime of the thin film sample.

(1) Step of Obtaining Thin Film Sample

A first step in the second embodiment is the step of obtaining a thin film sample. The thin film sample comprises at least a target polymer composition and a fluorescent probe including a fluorescent rare earth complex, and the fluorescent probe is localized at an interface with the substrate.

Also in the second embodiment, the types of the target polymer composition to be subjected to the measurement and the fluorescent rare earth complex used as the fluorescent probe are the same as those in first embodiment, and descriptions thereof are omitted in the second embodiment. Of the fluorescent rare earth complexes shown as examples in the first embodiment, ones with long fluorescence lifetimes can be preferably used. Since the fluorescence lifetime of tris(1,3-diphenyl-1,3-propanedionato)(1,10-phenanthroline)europium(III) complex is longer than those of ordinary organic dyes by three or more orders of magnitude, tris(1,3-diphenyl-1,3-propanedionato)(1,10-phenanthroline)europium(III) complex can be used particularly preferably also in the second embodiment.

Meanwhile, as the substrate constituting the thin film in the second embodiment, it is preferable to use a substrate satisfying a condition that the substrate is made of a material having a high refractive index n suitable for evanescent wave excitation of the fluorescent probe, in addition to the conditions described in the first embodiment. Preferred specific examples of substrates usable in the second embodiment include glass, sapphire, quartz, and lithium niobate. In addition, since the irradiation with the excitation light is conducted from the back side of the substrate, the substrate preferably has a shape such as a trapezoidal prism.

The thin film sample of the second embodiment can be prepared in the same manner as in the case of the thin film sample of the first embodiment. In this embodiment, the measurement of the evanescent excitation fluorescence lifetime makes it possible to obtain the information on the thermal mobility of molecular chains of the polymer only near the interface in the thin film sample in which the fluorescent probe is uniformly dispersed as in the case of the first embodiment.

(2) Step of Obtaining Correlation Between Fluorescence Lifetime and Temperature

A second step in the second embodiment is the step of obtaining a correlation between a fluorescence lifetime and a temperature. The second step comprises the steps of: measuring a fluorescence lifetime of the thin film sample obtained in the first step over a predetermined temperature range; and determining the $T_g$ on the basis of the measurement results.

In the step of measuring a fluorescence lifetime, the temperature range, the method, and the temperature intervals for the heating of the thin film sample are the same as those described in the first embodiment, and descriptions thereof are omitted.

The fluorescence lifetime can be measured by evanescent wave excitation of the fluorescent rare earth complex, and subsequent measurement of the fluorescence decay. The evanescent wave excitation of the fluorescent rare earth complex makes it possible to selectively obtain the information on the thermal mobility of the molecular chains at the interface between the substrate and the target polymer composition, and the $T_g$ at the interface between the substrate and the thin film sample, which is different from the bulk $T_g$ in the first embodiment, can be determined.

For the measurement of the fluorescence lifetime, it is possible to use a fluorescence lifetime-measuring apparatus including: an excitation light source with subpicosecond pulsed laser light; and fluorescence lifetime measurement means capable of measuring fluorescence decay on the order of nanoseconds with a time resolution of picoseconds. For the measurement in this embodiment, an apparatus which comprises a combination of a spectrometer and a streak camera and which performs time-resolved measurements at multiple wavelengths simultaneously is preferably selected as the fluorescence lifetime-measuring apparatus.

In the measurement, the substrate is irradiated with pulsed laser light from the back surface (the surface opposite from the surface on which the thin film sample is formed) at an incident angle $\theta_i$, which is larger than a critical angle $\theta_c$. Then, the evanescent excitation fluorescence lifetime is obtained at each measuring temperature. The excitation wavelength of the laser light can be determined in the same manner as in the case of the excitation wavelength of the fluorescence in the first embodiment. In addition, by adjusting the incident angle $\theta_i$, the $T_g$ at a position which is near the interface of the substrate and which is at a predetermined distance from the substrate can be determined. In this case, a person skilled in the art can determine, as appropriate, the relationship between the $\theta_i$ and the distance from the substrate based on theoretical calculation values. Note that, in the present invention, the position near the interface of the substrate for which the $T_g$ can be obtained by the measurement of the evanescent excitation fluorescence lifetime refers to the position at a distance of about 20 to 80 nm from the substrate, in general.

Note that the above-described evanescent wave excitation fluorescence lifetime is useful for evaluation of the thermal mobility of molecular chains at an interface; however, the present invention is not limited thereto. For example, the thermal mobility of molecular chains at an interface can also be evaluated by a measurement based on an evanescent wave excitation fluorescence depolarization method or the like.

Subsequently, the step of calculating the $T_g$ on the basis of the measurement results of the fluorescence lifetime is conducted. The step of calculating the $T_g$ comprises the steps of: plotting the measured value of the fluorescence lifetime at each measuring temperature against the temperature T (° C.); obtaining an approximate straight line in a high-temperature region and an approximate straight line in a low-temperature region on the basis of the plotted results; and obtaining, as the $T_g$, an intersection between the approximate straight line in the high-temperature region and the approximate straight line in the low-temperature region.

The step of obtaining the approximate straight line in the high-temperature region and the approximate straight line in the low-temperature region can be conducted in the same manner as in the first embodiment.

According to the second embodiment, the $T_g$ of the target polymer composition at the interface can be determined by using the fluorescent rare earth complex as a probe. An interface-dependent $T_g$ measurement method in the high-temperature region, which had not been established before, is now achieved by this embodiment for the first time. The measurement of the $T_g$ at an interface between a polymer composition and another kind of solid serves as a useful guide for development of various materials.

Note that, in this embodiment, when the irradiation with pulsed laser light is conducted with an incident angle $\theta_i$ smaller than the critical angle $\theta_c$, and the fluorescence lifetime is obtained at each measuring temperature, the bulk $T_g$ can be obtained as in the case of the first embodiment. The method according to this embodiment based on the fluorescence lifetime measurement is useful, because the $T_g$ of a colored resin can also be obtained, and hence the method can be applied to a wider variety of measurement targets.

Another aspect of the second embodiment provides an apparatus for determining an interface-dependent glass transition temperature of a polymer composition, the apparatus comprising: a heater configured to heat the thin film sample; an apparatus configured to measure an evanescent excitation fluorescence lifetime of the thin film sample; and optionally a computation processing unit. The heater, the apparatus configured to measure an evanescent excitation fluorescence lifetime, and the computation processing unit constituting this apparatus are the same as those described above. The glass transition temperature of a polymer composition at an interface can be obtained by operating this apparatus as described above.

Third Embodiment: Evaluation of Glass Transition Temperature of Polymer Composition at Desired Distance from Interface The present invention provides, in a third embodiment, a method for evaluating a physical property of a polymer composition at a predetermined distance from an interface between the target polymer composition and the substrate, the method comprising the steps of: obtaining a thin film sample which is formed on a substrate and which comprises at least: a fluorescent probe including a fluorescent rare earth complex having a melting point of 200° C. or higher; and a target polymer composition; and obtaining a relationship between a temperature and a fluorescence lifetime of the thin film sample.

(1) Step of Obtaining Thin Film Sample

A first step in the third embodiment is the step of obtaining a thin film sample. The thin film sample comprises at least: a target polymer composition and a fluorescent probe including a fluorescent rare earth complex. The fluorescent probe is localized at a predetermined distance from an interface with the substrate.

Also in the third embodiment, the types of the target polymer composition to be subjected to the measurement, the fluorescent rare earth complex used as the fluorescent probe, and the substrate are the same as those in the second embodiment, and descriptions thereof are omitted in the third embodiment.

In this embodiment, the thin film sample is formed, so that the fluorescent rare earth complex serving as the fluorescent probe in the thin film sample to be measured can be localized at a predetermined distance from the interface with the substrate. In an embodiment, the thin film sample can include two layers: a first layer which is located near the interface and in which the fluorescent rare earth complex and the target polymer composition are uniformly mixed; and a second layer which is located on the surface (on the side opposite from the substrate) and which contains no fluorescent rare earth complex but is made of only the target polymer composition. In this case, the first layer located near the interface and containing the fluorescent probe can be formed in a relatively small thickness of, for example, about 10 to 50 nm by the spin coating method described in the first embodiment, and the second layer can be formed by a spin coating method or a solvent evaporation method. When such a thin film sample is used, the $T_g$ near the interface can be determined.

Alternatively, the thin film sample can include three layers: a first layer located near the interface and made of only the target polymer composition; a second layer which is located at an intermediate position and in which the fluorescent rare earth complex and the target polymer composition are uniformly mixed; and a third layer located on the surface (on the side opposite from the substrate) and made of only the target polymer composition. In this case, by adjusting the thickness of the first layer formed in contact with the interface, the second layer, which is a layer containing the fluorescent probe, can be localized at a predetermined distance from the interface. In addition, the second layer may be formed by the spin coating method in a relatively small thickness of, for example, about 10 to 50 nm. By using the thin film sample in which the fluorescent probe is arranged with positional selectivity as described above, the $T_g$ can be determined at the predetermined distance from the interface.

In another embodiment, the thin film sample can include three layers: a first layer which is located near the interface and which does not contain the fluorescent rare earth complex but is made of only the target polymer composition layer; a second layer which is localized at a predetermined distance from an interface with the substrate and which is a vapor-deposition film of the fluorescent rare earth complex; and a third layer which is located near the surface and which does not contain the fluorescent rare earth complex but is made of only the target polymer composition. The first layer and the third layer, which are made of only the target polymer composition, can be formed by the spin coating method or the solvent evaporation method described in the first embodiment. On the other hand, the vapor-deposition film layer of the fluorescent rare earth complex can be layered on the first layer by an ordinary vapor deposition method. The thickness of the vapor-deposition film is, for example, 100 nm or smaller and preferably 10 nm or smaller, but is not smaller than a thickness in which at least a single molecule of the fluorescent rare earth complex can be present. By adjusting the thickness of the first layer formed in contact with the interface, the second layer of the fluorescent rare earth complex can be localized at a predetermined distance from the interface. By using the thin film sample in which the fluorescent probe is arranged with positional selectivity, the $T_g$ can be determined at a predetermined distance from the interface.

(2) Step of Obtaining Correlation Between Fluorescence Lifetime and Temperature

A second step is the step of obtaining a correlation between a fluorescence lifetime and a temperature. The second step comprises the steps of: measuring a fluorescence lifetime of the thin film sample obtained in the first step over a predetermined temperature range, and determining the $T_g$ on the basis of the measurement results. In this embodiment, the step of measuring a fluorescence lifetime is different from that in the second embodiment in that this step can be conducted by measuring ordinary transmitted light. Also in this case, the fluorescence lifetime-measuring apparatus and the measurement conditions such as the wavelength of the laser light used for the excitation are generally the same as those in the second embodiment. The step of determining the Tg on the basis of the measurement results can be conducted in the same manner as in the second step in the second embodiment, and descriptions thereof are omitted.

In the third embodiment, the glass transition temperature of a polymer composition at a desired distance from the interface can be obtained. Obtaining such information is particularly useful for designing the particle diameter and the amount of a filler added to improve only the heat resistance of an already-existing sealant, adhesive, or the like.

In addition, another aspect of the third embodiment provides an apparatus for determining an interface-dependent glass transition temperature of a polymer composition, the apparatus comprising: a heater configured to heat the thin film sample; an apparatus configured to measure a fluorescence lifetime of the thin film sample; and optionally a computation processing unit. The heater, the apparatus configured to measure a fluorescence lifetime, and the computation processing unit constituting this apparatus are the same as those described above. By operating this apparatus as described above, the glass transition temperature of a polymer composition at a predetermined distance from an interface with a substrate can be obtained.

EXAMPLES

Hereinafter, the present invention is described in further detail based on Examples; however, the present invention is not limited to Examples below.

Example 1: $T_g$ Measurement of Polymer Thin Film (Inside Film)

Polystyrene (PS), polymethyl methacrylate (PMMA), and a cyclic olefin resin (Arton (registered trademark) manufactured by JSR Corporation) were used as target polymer compositions. The chemical structures of the monomers of these polymers are shown below. Table 1 shows the number average molecular weight ($M_n$), the molecular-weight distribution index (PDI), and the $T_g$ evaluated on the basis of a differential scanning calorimetry (DSC) measurement of each of the polymer compositions used as the samples.

[Chem. 1]

TABLE 1

| Polymer | $M_n$/g mol$^{-1}$ | $M_w/M_n$ | $T_g$/° C. |
|---|---|---|---|
| PS | 1.79 × 10$^5$ | 1.03 | 103 |
| PMMA | 4.4 × 10$^4$ | 1.02 | 130 |
| Arton (registered trademark) | 4.5 × 10$^4$ | 2.20 | 149 |

As a fluorescent probe, tris(1,3-diphenyl-1,3-propanedionato)(1,10-phenanthroline)europium(III) (Eu complex, manufactured by Tokyo Chemical Industry Co., Ltd.) was used. The structure of the Eu complex used is shown below.

[Chem. 2]

Mixtures were prepared by mixing the Eu complex at a mass fraction of 5% by mass with each of PS, PMMA, and Arton (registered trademark). Here, the ratio in % by mass of the Eu complex is that of the Eu complex relative to the total mass of the mixture. Each of the mixtures was dissolved in toluene to prepare 2% by mass solutions. PS, PMMA, and Arton (registered trademark) films in which the Eu complex was dispersed were each formed on a sapphire prism from the corresponding toluene solution by the solvent evaporation method. Subsequently, a heat treatment was conducted on the PS film in which the Eu complex was dispersed and the PMMA film in which the Eu complex was dispersed. Conditions of the heat treatment on the PS film in which the Eu complex was dispersed were 130° C. and 24 hours under a vacuum. Conditions of the heat treatment on the PMMA film in which the Eu complex was dispersed were 130° C. and 24 hours under a vacuum. The Arton (registered trademark) film in which the Eu complex was dispersed was not subjected to the heat treatment, but was dried at 25° C. for 24 hours under a vacuum. The film thickness of each of the thin film samples subjected to the vacuum heating or the vacuum drying from which the toluene solvent was removed was approximately 5 μm.

Figure 1:
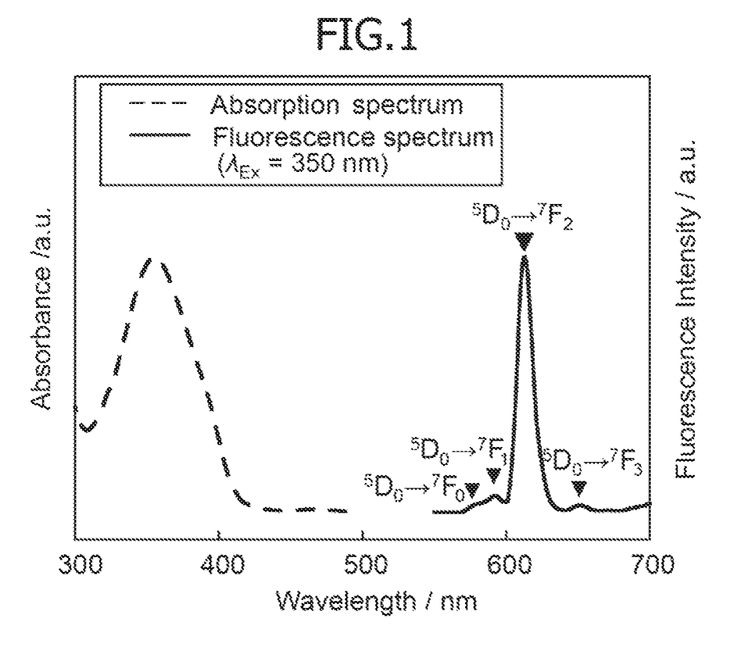
FIG. 1 is an ultraviolet (UV)-visible (vis) absorption spectrum and a fluorescence spectrum of a Eu complex used in Examples.

Based on absorption spectroscopy, ultraviolet (UV)-visible (vis) absorption spectra of the thin film samples were evaluated. In addition, based on fluorescence spectroscopy, fluorescence spectra of the thin film samples at various temperatures were evaluated. The apparatuses used for the measurement were U-4100 (Hitachi High-Technologies Corporation) and F-4500 (Hitachi High-Technologies Corporation). FIG. 1 shows the results. Based on the evaluation results of the absorption spectra, 350 nm, which was the maximum absorption wavelength, was employed as the excitation wavelength ($\lambda_{Ex}$). In the fluorescence spectra, peaks were observed at 580 nm, 592 nm, 613 nm, and 652 nm, which are assignable to $^5D_0 \rightarrow{}^7F_0$, $^5D_0 \rightarrow{}^7F_1$, $^5D_0 \rightarrow{}^7F_2$, and $^5D_0 \rightarrow{}^7F_3$ transitions, respectively.

Figure 2:
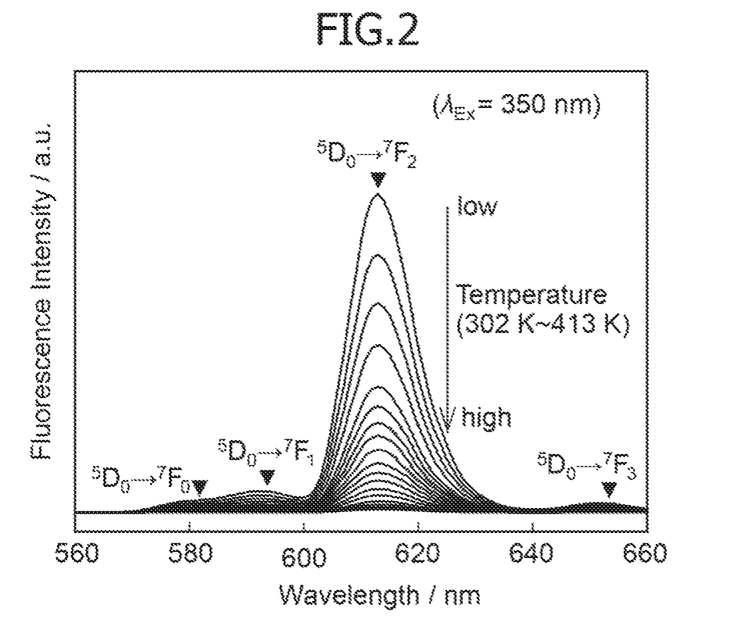
FIG. 2 is a graph showing the temperature dependence of a fluorescence spectrum of a PS film in which the Eu complex used in Examples was dispersed.

Subsequently, the temperature dependence of the fluorescence spectrum of the PS film in which the Eu complex was dispersed was measured. The temperature of the thin film sample was controlled by sandwiching the prism between ceramic heaters each having a built-in thermocouple (small aluminum nitride heaters (WATLOW ULTRAMIC (WLAN-5) (SAKAGUCHI E.H VOC CORP.)) from the above and below, and the measurement temperature ranged from room temperature to $T_g$+30° C. The temperature intervals of the measurement were 10° C. from the room temperature to Tg–30° C., and 5° C. at or above $T_g$–30° C. FIG. 2 shows the results. The wavelengths of the peaks corresponding to the transitions were constant irrespective of the temperature, but the fluorescence intensities decreased with the rise in temperature.

Figure 3:
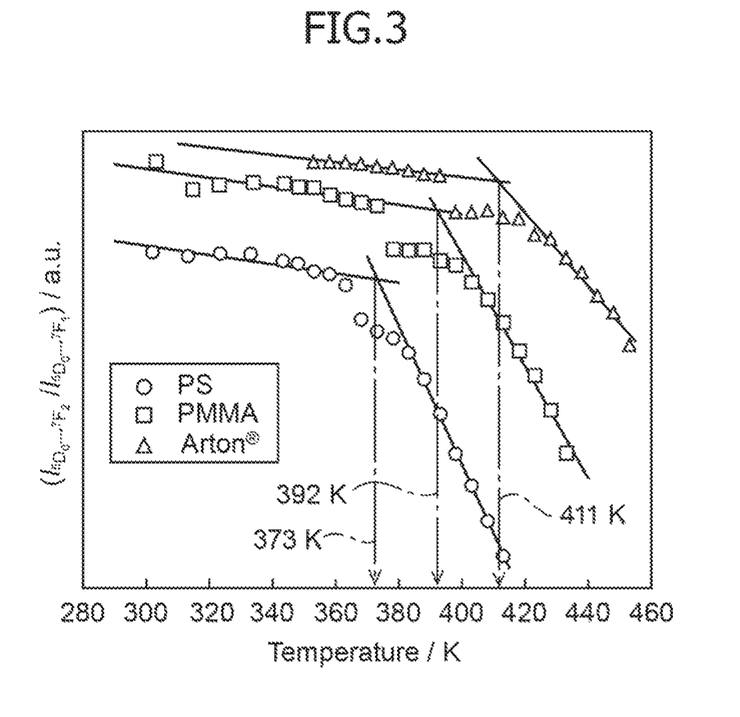
FIG. 3 is a graph showing the temperature dependence of the fluorescence intensity ratio R ($I_{5D0 \to 7F2}/I_{5D0 \to 7F1}$) of a PS film, a PMMA film, and an Arton (registered trademark) film in each of which the Eu complex used in Examples was dispersed.

An attempt was made to extract information on the thermal motions of the matrix polymer from the intensity ratio R ($I_{5D0 \rightarrow 7F2}/I_{5D0 \rightarrow 7F1}$) of the $^5D_0 \rightarrow{}^7F_2$ transition based on the electric dipole transition, which presumably responded to local motions of the polymer, to the $^5D_0 \rightarrow{}^7F_1$ transition based on the magnetic dipole transition, which presumably did not respond to the local motions. FIG. 3 shows the temperature dependence of the intensity ratio R of each of the PS film, the PMMA film, and the Alton (registered trademark) film in which the Eu complex was dispersed. In each of the films, the intensity ratio R gently decreased with the rise in temperature, and sharply decreased at and above a certain temperature. For the PS, PMMA, and Arton (registered trademark) films, the temperatures at the intersections of two approximate straight lines on the low-temperature side and the high-temperature side were 100° C., 119° C., and 138° C., respectively. The change in slope means that the dynamic environment surrounding the probe molecules changed. The temperatures at the intersections were substantially equal to the $T_g$s evaluated based on DSC measurement. The above-described results have demonstrated that the Eu complex is effective as a fluorescent probe for evaluating the thermal mobility of a polymer composition.

Since the excitation light passed through each film under the conditions of this example, it is conceivable that the obtained information reflected the molecular motions of the film as a whole. From the result that the $T_g$ obtained by this experiment was equal to the $T_g$ obtained by the DSC measurement, it is conceivable that the Eu complex was well dispersed in the polymer, and that the surface of the thin film and the vicinity of the interface with the substrate exerted a relatively small influence on the obtained $T_g$.

Example 2: $T_g$ Measurement at Polymer Composition/Substrate Interface

The glass transition temperatures of cured resins using ordinary epoxy resin compositions as target polymer compositions were evaluated. Table 2 shows the results. As the fluorescent probe, the same Eu complex as in Example 1 was used. The same substrates as those in Example 1 were used. The content of the Eu complex in the thin film samples, and the thickness of the thin film samples were also the same as those in Example 1. The thin film samples were prepared with the Eu complex being uniformly dispersed in each epoxy resin composition.

In Sample 1, a his A-type epoxy resin (trade name: "JER828," manufactured by Mitsubishi Chemical Corporation, epoxy equivalent weight: 194), which was known as an ordinary epoxy resin, was used. The curing agent used was a modified amine-type curing agent (trade name. "JER Cure 113," manufactured by Mitsubishi Chemical Corporation), which was an ordinary curing agent. The bulk of sample 1 was measured by DSC, and the $T_g$ was determined to be 149° C. Based on the second embodiment of the present invention, $T_g$ measurement was conducted by the evanescent method. In the measuring apparatus here, a fundamental wave generated by a mode-locked titanium:sapphire laser (Tsunami, Spectra-Physics) at a wavelength of 770 nm with a pulse repetition frequency of 80 MHz was used as a light source. The pulse repetition frequency of the fundamental wave was changed to 8 MHz with a pulse selector (Model 3986, Spectra-Physics), and a second harmonic wave at 385 nm was generated with a frequency doubler (Model 3980, Spectra-Physics). This second harmonic wave was caused to be incident on the sample as an excitation light source. The fluorescence generated by the light excited fluorescent probe was concentrated by using two plano-convex lenses, and subjected to time-resolved measurements simultaneously at multiple wavelengths by using a combination of a multichannel spectrometer (C5094, Hamamatsu Photonics K.K.) and a streak camera (C4334, Hamamatsu Photonics K.K.). The heaters used for adjusting the temperature of thin film sample, the measurement temperature range, and the measurement temperature intervals were the same as those in Example 1. The thin film sample was formed by mixing the Eu complex at a mass fraction of 5% by mass with an uncured composition (equivalence ratio=1) of the bis A-type epoxy resin and the modified amine-type curing agent, and forming a film having a film thickness of 0.5 µm on the substrate by screen printing. A measurement with an incident angle θ, of 80° showed that the $T_g$ at a position 30 nm away from the substrate was 162° C. In addition, a measurement with an incident angle θ, of 62° conducted in the same manner showed that the $T_g$ at a position 80 nm away from the substrate was 154° C.

It is generally believed that molecular motions are inhibited at a joint portion between a resin and a substrate because of chemical bonding between filler and an epoxy resin or the like. It is known that the $T_g$ at the joint portion is higher than that of the resin in the bulk, and the closer to the interface, the more the value increases. The measurement results in this example are in agreement with this knowledge, and it can be understood that the $T_g$ near the interface was accurately measured by the evanescent method.

In addition, as sample 2, a thin film sample was prepared in the same manner as in the case of sample 1, except that a trifunctional epoxy resin (trade name: "JER630," manufactured by Mitsubishi Chemical Corporation, epoxy equivalent weight: 105), which was a generally known multifunctional epoxy resin, was used. The bulk of sample 2 was measured by DSC, and the $T_g$ was determined to be 190° C. By employing the same apparatus and the same measurement conditions as those for sample 1, the $T_g$ was measured by the evanescent method. The results showed that the $T_g$ at a position 30 nm away from the substrate was 225° C. Likewise, the $T_g$ at a position 80 nm away from the substrate was 218° C. Also from the measurement results of sample 2, it can be understood that the $T_g$ near the interface was accurately measured by the evanescent method, and further it has been found that the measurement can be conducted also in a temperature region exceeding 200° C.

TABLE 2

|  |  | Sample 1 | Sample 2 |
|---|---|---|---|
| Resin composition | Epoxy resin 1 | 75.8 |  |
|  | Epoxy resin 2 |  | 62.2 |
|  | Curing agent | 24.2 | 37.8 |
| Curing conditions |  | 80° C. × 1 hr | 80° C. × 3 hr |
|  |  | 150° C. × 3 hr | 150° C. × 6 hr |
| $T_g$ of cured resin (° C.) | DSC (bulk) | 149 | 190 |
|  | Evanescent method (30 nm from substrate) | 162 | 225 |
|  | Evanescent method (80 nm from substrate) | 154 | 218 |

INDUSTRIAL APPLICABILITY

The method for evaluating a physical property of a polymer composition according to the present invention makes it possible to easily evaluate the bulk Tg of a high-$T_g$ material such as a super engineering plastic, which is generally defined as one usable at 150° C. or above for a long period, and also makes it possible to the $T_g$ at an interface between a high-$T_g$ material and another kind of solid. For example, it is possible to evaluate the molecular motions of a polymer in an active layer sandwiched between electrodes in an organic thin film solar cell, or the $T_g$ of a colored sample at an interface with a substrate. Hence, this method can be used as a tool useful for development of a polymer material for a high-temperature region.

The invention claimed is:

1. A method for determining a glass transition temperature of a polymer composition, comprising:
    obtaining the glass transition temperature of the polymer composition in a film sample based on a correlation between a temperature and a fluorescent characteristic of the film sample, wherein the film sample is disposed on a substrate, the film sample comprising the polymer composition and a fluorescent probe having a fluorescent rare earth complex having a melting point of 200° C. or higher, wherein the fluorescence characteristic is one selected from the group consisting of an intensity ratio between a fluorescence intensity of electric dipole transition of the polymer composition and a fluorescence intensity of magnetic dipole transition of the polymer composition, and a fluorescence lifetime.

2. The method according to claim 1, wherein the fluorescent probe comprises a fluorescent rare earth complex containing a trivalent lanthanoid ion as a central metal ion.

3. The method for evaluating a physical property of a polymer composition according to claim 2, wherein
    the fluorescent probe is uniformly dispersed in the film sample,
    wherein the fluorescent characteristic is the intensity ratio, and
    wherein a bulk glass transition temperature of the polymer composition is the glass transition temperature obtained from the correlation between the temperature of the film sample and the intensity ratio.

4. The method for evaluating a physical property of a polymer composition according to claim 2, wherein
    the fluorescent probe is uniformly dispersed in the film sample,
    wherein the fluorescent characteristic is the fluorescence lifetime, and
    wherein a glass transition temperature at an interface between the polymer composition and the substrate is the glass transition temperature obtained from the correlation between the temperature of the film sample and the fluorescence lifetime.

5. The method according to claim 4, wherein
    the fluorescence lifetime is an evanescent excitation fluorescence lifetime.

6. The method for evaluating a physical property of a polymer composition according to claim 2, wherein
    the fluorescent probe in the film sample is localized at a predetermined distance from an interface with the substrate,
    wherein the fluorescent characteristic is the fluorescence lifetime, and
    wherein a glass transition temperature of the polymer composition at the predetermined distance from the interface between the polymer composition and the substrate is the glass transition temperature obtained from the correlation between the temperature of the film sample and the fluorescence lifetime.

7. The method according to claim 1, wherein
    the fluorescent probe is uniformly dispersed in the film sample,
    wherein the fluorescent characteristic is the intensity ratio, and
    wherein a bulk glass transition temperature of the polymer composition is the glass transition temperature obtained from the correlation between the temperature of the film sample and the intensity ratio.

8. The method according to claim 1, wherein
    the fluorescent probe is uniformly dispersed in the film sample,
    wherein the fluorescent characteristic is the fluorescence lifetime, and
    wherein a glass transition temperature at an interface between the polymer composition and the substrate is the glass transition temperature obtained from the correlation between the temperature of the film sample and the fluorescence lifetime.

9. The method according to claim 8, wherein the fluorescence lifetime is an evanescent excitation fluorescence lifetime.

10. The method according to claim 1,
    wherein the fluorescent probe in the film sample is localized at a predetermined distance from an interface with the substrate,
    wherein the fluorescent characteristic is the fluorescence lifetime, and
    wherein a glass transition temperature of the polymer composition at the predetermined distance from the interface between the polymer composition and the substrate is the glass transition temperature obtained from the correlation between the temperature of the film sample and the fluorescence lifetime.

11. The method according to claim 1, wherein
    the fluorescent rare earth complex includes a trivalent lanthanoid ion as a central metal ion,
    wherein the fluorescent probe is uniformly dispersed in the film sample, wherein the glass transition temperature is a bulk glass transition temperature of the polymer composition, and wherein obtaining the bulk glass transition temperature comprises:

obtaining the intensity ratio ($R_T$) between a fluorescence intensity of electric dipole transition of the polymer composition and a fluorescence intensity of magnetic dipole transition of the polymer composition as a function of temperature, the temperature ranging from a first region below the bulk glass transition temperature to a second region above the bulk glass transition temperature;

fitting an approximate straight line in the first region and an approximate straight line in the second region using the obtained $R_T$; and obtaining the bulk glass transition temperature at the intersection between the approximate straight line in the first region and the approximate straight line in the second region.

12. The method according to claim 1, wherein the fluorescent rare earth complex includes a trivalent lanthanoid ion as a central metal ion, wherein the fluorescent probe is uniformly dispersed in the film sample, wherein the glass transition temperature is a glass transition temperature of the polymer composition at an interface, and wherein obtaining the glass transition temperature at the interface comprises:

measuring the fluorescence lifetime of the film sample as a function of temperature, the temperature ranging from a first region below the glass transition temperature to a second region above the glass transition temperature;

fitting an approximate straight line in the first region and an approximate straight line in the second region using the measured fluorescence lifetime; and obtaining the glass transition temperature at the interface at an intersection between the approximate straight line in the first region and the approximate straight line in the second region.

13. The method according to claim 1, wherein the fluorescent rare earth complex includes a trivalent lanthanoid ion as a central metal ion, wherein the fluorescent probe in the film sample is localized at a predetermined distance from an interface with the substrate, wherein the glass transition temperature is a glass transition temperature of the polymer composition at a predetermined distance from the interface with the substrate, and wherein obtaining the glass transition temperature at the predetermined distance comprises:

measuring the fluorescence lifetime of the film sample as a function of temperature, wherein the temperature ranges from a first region below the glass transition temperature to a second region above the glass transition temperature;

fitting an approximate straight line in the first region and an approximate straight line in the second region based on the measured fluorescence lifetime; and obtaining the glass transition temperature at the predetermined distance at an intersection between the approximate straight line in the first region and the approximate straight line in the second region.

* * * * *